United States Patent
Wald et al.

(10) Patent No.: US 10,359,481 B2
(45) Date of Patent: *Jul. 23, 2019

(54) SYSTEM AND METHOD FOR PORTABLE MAGNETIC RESONANCE IMAGING USING A ROTATING ARRAY OF PERMANENT MAGNETS

(71) Applicants: Lawrence L. Wald, Cambridge, MA (US); Clarissa Zimmerman, Charlestown, MA (US); Jason Stockmann, Cambridge, MA (US)

(72) Inventors: Lawrence L. Wald, Cambridge, MA (US); Clarissa Zimmerman, Charlestown, MA (US); Jason Stockmann, Cambridge, MA (US)

(73) Assignee: The General Hospital Corporation, Boston, MA (US)

( * ) Notice: Subject to any disclaimer, the term of this patent is extended or adjusted under 35 U.S.C. 154(b) by 1238 days.

This patent is subject to a terminal disclaimer.

(21) Appl. No.: 14/408,187

(22) PCT Filed: Oct. 22, 2012

(86) PCT No.: PCT/US2012/061341
§ 371 (c)(1),
(2) Date: Dec. 15, 2014

(87) PCT Pub. No.: WO2013/187924
PCT Pub. Date: Dec. 19, 2013

(65) Prior Publication Data
US 2015/0177343 A1    Jun. 25, 2015

(51) Int. Cl.
*G01V 3/00* (2006.01)
*G01R 33/34* (2006.01)
(Continued)

(52) U.S. Cl.
CPC ...... *G01R 33/34092* (2013.01); *A61B 5/0042* (2013.01); *A61B 5/055* (2013.01);
(Continued)

(58) Field of Classification Search
CPC .................................................. G01R 33/383
(Continued)

(56) References Cited

U.S. PATENT DOCUMENTS 4,498,048 A    2/1985    Lee et al.
6,806,712 B2 *  10/2004   Akgun ................. A61B 5/055
                                                324/309

(Continued)

FOREIGN PATENT DOCUMENTS

DE        19912428 C2    1/2001
EP        2226815         9/2010
(Continued)

OTHER PUBLICATIONS

Chamberlain, et al., RASER: A New Ultrafast Magnetic Resonance Imaging Method, Magnetic Resonance in Medicine, 2007, 58(4):794-799.

(Continued)

*Primary Examiner* — Louis M Arana
(74) *Attorney, Agent, or Firm* — Quarles & Brady LLP (57) ABSTRACT

A portable magnetic resonance imaging ("MRI") system that uses static magnetic field inhomogeneities in the main magnet for encoding the spatial location of nuclear spins is provided. Also provided is a spatial-encoding scheme for a low-field, low-power consumption, light-weight, and easily transportable MRI system. In general, the portable MRI system spatially encodes images using spatial inhomogeneities in the polarizing magnetic field rather than using gradient fields. Thus, an inhomogeneous static field is used to polarize, readout, and encode an image of the object. To provide spatial encoding, the magnet is rotated around the object to generate a number of differently encoded measurements. An image is then reconstructed by solving for the object most consistent with the data.

30 Claims, 5 Drawing Sheets

(51) Int. Cl.
| | |
|---|---|
| A61B 5/055 | (2006.01) |
| A61B 5/00 | (2006.01) |
| G01R 33/383 | (2006.01) |
| G01R 33/28 | (2006.01) |
| G01R 33/46 | (2006.01) |
| G01R 33/38 | (2006.01) |
| G01R 33/48 | (2006.01) |
| G01R 33/44 | (2006.01) |

(52) U.S. Cl.
CPC ........... *G01R 33/28* (2013.01); *G01R 33/383* (2013.01); *G01R 33/46* (2013.01); *G01R 33/3802* (2013.01); *G01R 33/445* (2013.01); *G01R 33/4824* (2013.01)

(58) Field of Classification Search
USPC ........................................ 324/318, 319, 320
See application file for complete search history.

(56) References Cited

U.S. PATENT DOCUMENTS

| | | | | |
|---|---|---|---|---|
| 7,609,062 | B2* | 10/2009 | Roland | A61B 5/0555 324/318 |
| 8,159,222 | B2 | 4/2012 | King et al. | |
| 8,525,627 | B2* | 9/2013 | Higuchi | H01F 7/0284 310/154.01 |
| 9,910,115 | B2* | 3/2018 | Wald | G01R 33/383 |
| 2009/0128272 | A1 | 5/2009 | Hill | |
| 2017/0038451 | A1* | 2/2017 | Ristic | G01R 33/3802 |

FOREIGN PATENT DOCUMENTS

| | | |
|---|---|---|
| JP | S6297544 A | 5/1987 |
| JP | S63132642 A | 6/1988 |

OTHER PUBLICATIONS

Deng, et al., 1D RF Phase Gradient Coil for TRASE RF Imaging, Proc. Intl. Soc. Mag. Reson. Med., 2011, 19:1813.

Hennig, et al., Parallel Imaging in Non-Bijective, Curvilinear Magnetic Field Gradients: A Concept Study, Magn. Reson. Mater. Phy., 2008, 21(1-2):5-14.

Pipe, Spatial Encoding and Reconstruction in MRI with Quadratic Phase Profiles, Magnetic Resonance in Medicine, 1995, 33(1):24-33.

Schultz, et al., Radial Imaging With Multipolar Magnetic Encoding Fields, IEEE Transactions on Medical Imaging, 2011, 30(12):2134-2145.

Sharp, et al., MRI Using Radiofrequency Magnetic Field Phase Gradients, Magnetic Resonance in Medicine, 2010, 63(1):151-161.

Zimmerman, et al., Design and Construction of a Halbach Array Magnet for Portable Brain MRI, Proc. Intl. Soc. Mag. Reson. Med., 2012, 20:2575.

The International Search Report and Written Opinion dated Mar. 21, 2013 for International Application No. PCT/US2012/061341.

* cited by examiner

SYSTEM AND METHOD FOR PORTABLE MAGNETIC RESONANCE IMAGING USING A ROTATING ARRAY OF PERMANENT MAGNETS

STATEMENT REGARDING FEDERALLY SPONSORED RESEARCH

This invention was made with government support under W81XWH-11-2-0076 awarded by The U.S. Army Medical Research and Materiel Command. The government has certain rights in the invention.

CROSS-REFERENCE TO RELATED APPLICATIONS

This application represents the national stage entry of PCT International Application No. PCT/US2012/061341 on Oct. 22, 2012 and claims the benefit of U.S. Provisional Patent Application No. 61/660,278 filed Jun. 15, 2012, and entitled "MRI Encoding with an Inhomogeneous Magnetic Field."

BACKGROUND OF THE INVENTION

The field of the invention is systems and methods for magnetic resonance imaging ("MRI"). More particularly, the invention relates to systems and methods for portable MRI using an inhomogeneous magnetic field for spatial encoding.

A conventional MRI scanner uses several different magnetic fields to produce an image. One field is a static, highly uniform magnetic field that is used to polarize the nuclear magnetization and in which a free-induction decay ("FID") signal is read-out. Another field is a radio frequency ("RF") pulsed field to initiate the FID. Also, one or more gradient fields are used to encode the spatial location from which the FID originates, thereby spatially encoding the resulting image. The gradient fields are spatially changing (e.g., linear with position) gradient fields that modulate the spin phase as a function of position. As a result of the modulate spin phase, the location of the signal is encoded as the Fourier transform of the acquired signal. Sometimes a non-homogeneous pre-polarization field is used to boost the initial magnetization, which is then read-out in a uniform, lower strength field.

Much of the size and complexity of an MRI system derives from the fact that typical clinical MRI systems require a very homogeneous static magnetic field and very high-power linear gradient fields. Thus, current MRI systems are limited to hospital settings due to the weight and fragility of highly homogeneous superconducting or permanent magnets. An additional burden is the need for hundreds of amps of current to power the gradient fields. To make the MRI system portable, a new type of MR encoding scheme is needed. It has not been sufficient to simply "shrink down" current designs.

A portable MR system has the potential to quickly detect brain injury at the site of injury. For example hemorrhage detection is critical for both stroke patients and traumatic brain injury victims. In stroke, rapid distinction between a hemorrhagic and non-hemorrhagic event could allow administration of a clot-busting drug such as tPA (tissue plasminogen activator) in an ambulance prior to transportation to the hospital, perhaps advancing this time-sensitive treatment by up to an hour. Subdural hemorrhage (or hematoma) is a form of traumatic brain injury, in which blood gathers between the dura and arachnoid mater (in meningeal layer) and is likely to be visualized on course resolution (e.g. 5 mm) T1 images. Rapid diagnostics of the hemorrhage in the field could substantially accelerate treatment by adverting a "wait and see" approach. After brain surgery, some patients develop a hemorrhage that must be treated immediately. A bedside MRI in a neuro-ICU would allow frequent checks for the development of such hemorrhaging.

Others have disclosed portable nuclear magnetic resonance spectrometers; however, even these systems still make use of conventional encoding schemes that require gradients.

It would therefore be desirable to provide a portable MRI system that does not require the use of magnetic field gradient coils to provide spatial encoding of magnetic resonance signals.

SUMMARY OF THE INVENTION

The present invention overcomes the aforementioned drawbacks by providing a portable magnetic resonance imaging ("MRI") system that uses its naturally inhomogeneous magnetic field to spatially encode magnetic resonance signals.

It is an aspect of the invention to provide a portable MRI system that includes a magnet assembly, a rotator, a radio frequency ("RF") coil, and a controller. The magnet assembly includes a plurality of permanent magnets and a support. Each of the plurality of permanent magnets extend from a proximal end to a distal end along a longitudinal axis of the magnet assembly. The support is configured to hold the plurality of permanent magnets in an annular arrangement so as to define a region configured to receive an object to be imaged. The support is also configured to hold the plurality of permanent magnets such that the permanent magnets generate a magnetic field that varies with spatial location in a plane transverse to the longitudinal axis of the magnet assembly. The rotator is coupled to the magnet assembly and configured to rotate the magnet assembly about its longitudinal axis through a plurality of different rotation angles. The RF coil is configured to generate RF energy and receiving magnetic resonance signals from an object positioned in the magnet assembly. The controller configured to direct the rotator to rotate the magnet assembly through the plurality of different rotation angles and to direct the RF coil to generate RF energy and receive responsive magnetic resonance signals at each rotation angle.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

A portable magnetic resonance imaging ("MRI") system that uses static magnetic field inhomogeneities in the main magnet for encoding the spatial location of nuclear spins is provided. Also provided is a spatial-encoding scheme for a low-field, low-power consumption, light-weight, and easily transportable MRI system. In general, the portable MRI system of the present invention employs spatial inhomogeneities in the polarizing $B_0$ magnetic field rather than gradient fields to spatially encode images. Thus, in the system of the present invention, an inhomogeneous static field is used to polarize, readout, and encode an image of the object. To provide spatial encoding, the magnet is rotated around the object to generate a number of differently encoded measurements. An image is then reconstructed by solving for the object most consistent with the data, for example in the least-squares sense, with or without the use of constrains or prior knowledge (other than the spatial map of the $B_0$ field).

The portable MRI system of the present invention may be used to detect hemorrhage in emergency situations, to monitor for hemorrhage in the intensive care unit ("ICU") after brain surgery at a patient's bedside, or to detect hemorrhagic stroke at an early stage. The latter application is particularly useful as the early detection of hemorrhagic stroke can accelerate the application of an anti-thrombolytic agent, thereby improving the patient's clinical outcome.

Figure 1:
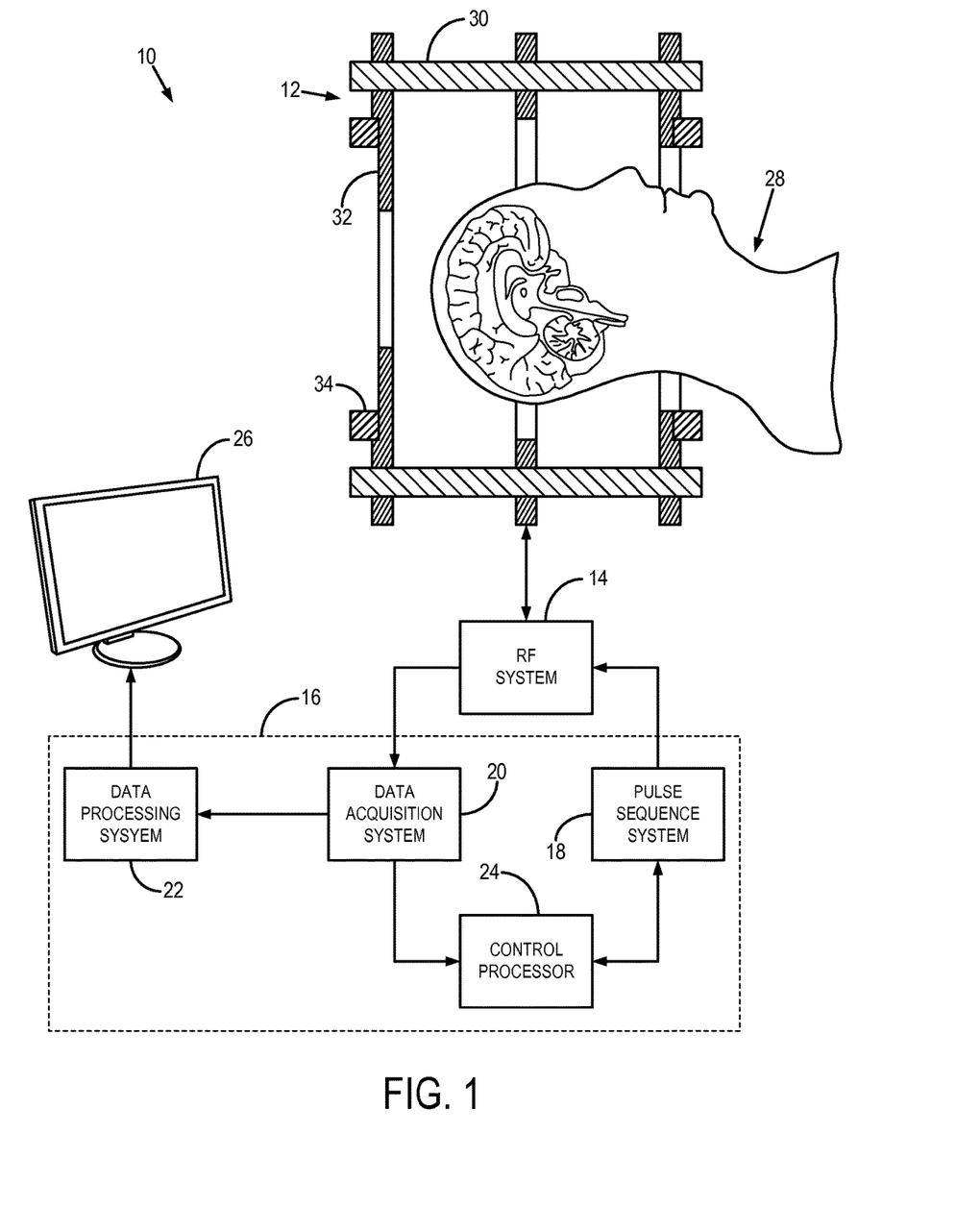
FIG. 1 is a block diagram of an example of a portable magnetic resonance imaging ("MRI") system in accordance with embodiments of the present invention.

As seen in FIG. 1, the portable MRI system 10 of the present invention generally includes a magnet assembly 12, a radio frequency ("RF") system 14, and a controller 16. The controller 16 may include, for example, a pulse sequence system 18, a data acquisition system 20, a data processing system 22, and a control processor 24. The portable MRI system 10 may also include a display 26 for viewing images of the subject 28 obtained with the portable MRI system 10 and for providing a user interface between the operator and the controller 16. The portable MRI system 10 does not require gradient coils or high-power gradient amplifiers. Thus, the RF system 14 and controller 16 may be constructed of small signal electronics an a small RF power amplifier, all of which can easily fit in the back of an ambulance.

Figure 2:
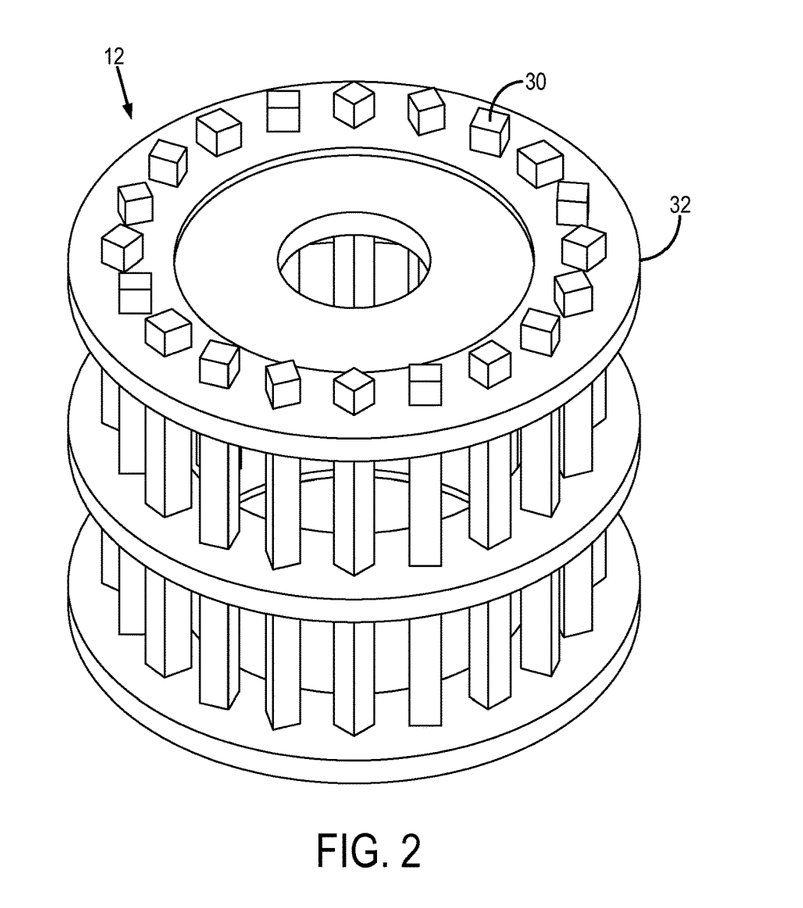
FIG. 2 is an example of a magnet assembly that forms a part of the portable MRI system of the present invention.
Figure 3:
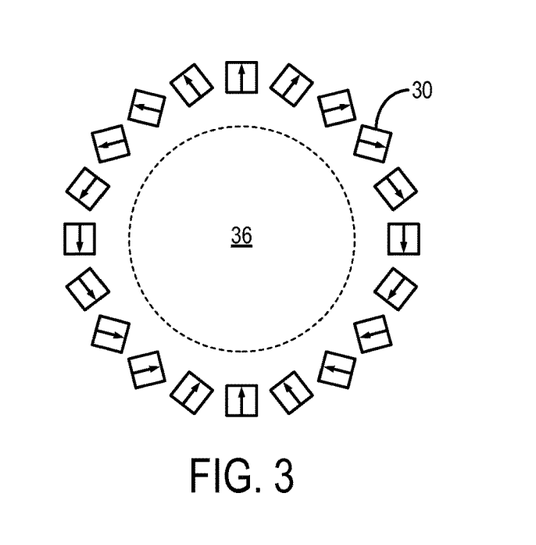
FIG. 3 is an illustration of an example arrangement of the permanent magnets in the magnet assembly of FIG. 2, in which the permanent magnets are arranged in an annular Halbach array.
Figure 4:
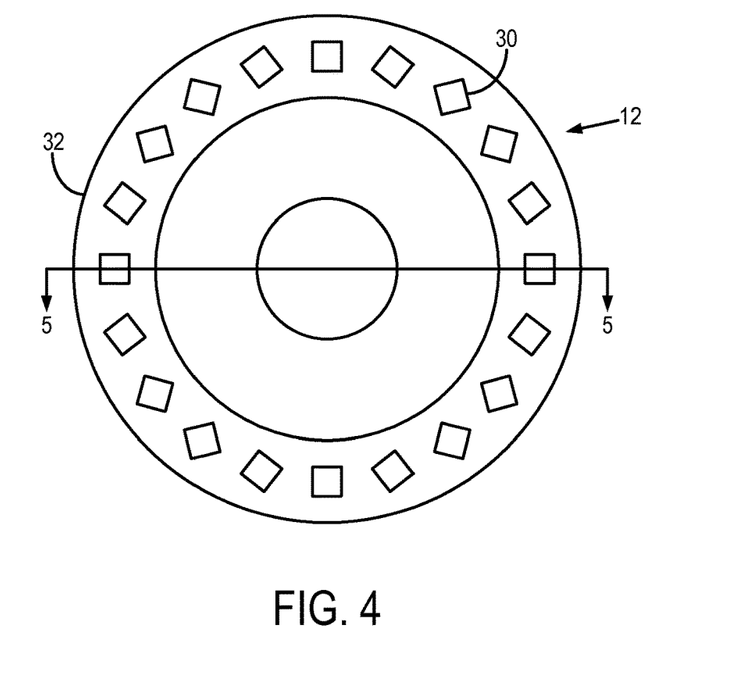
FIG. 4 is a plan view of the magnet assembly of FIG. 2.
Figure 5:
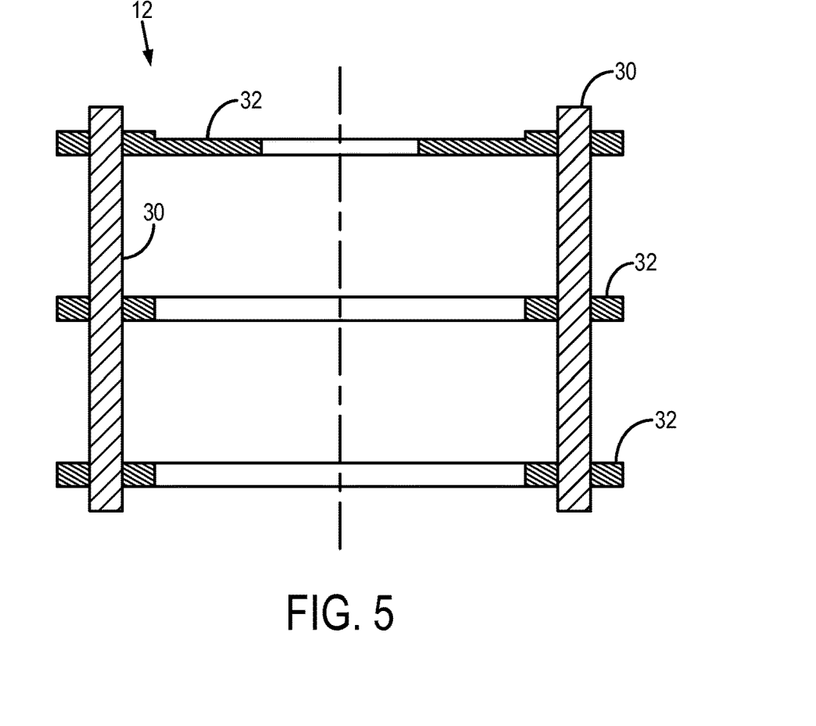
FIG. 5 is a cross-section of the magnet assembly of FIG. 2.
Figure 6:
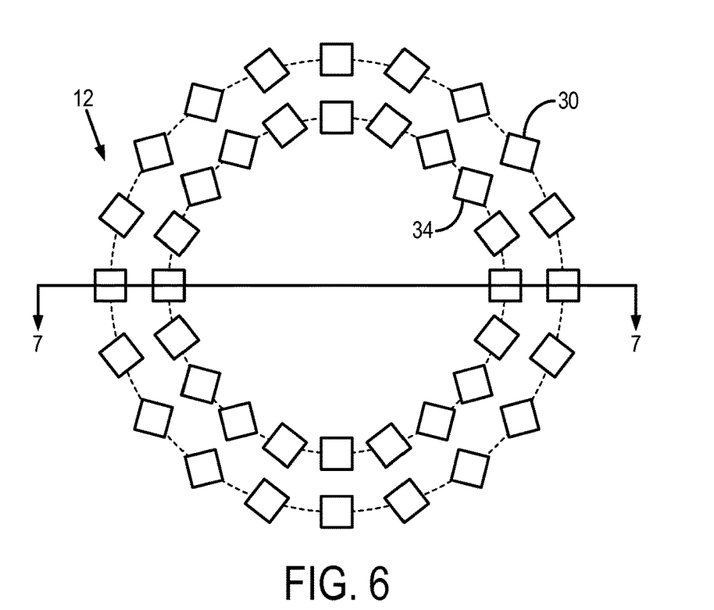
FIG. 6 is an example configuration of permanent magnets that may form a part of a magnet assembly used in a portable MRI system in accordance with the present invention, in which the permanent magnets include end-ring magnets that control uniformity of the magnetic field produced by the magnet assembly.

The magnet assembly 12 generally includes a plurality of permanent magnets 30 arranged in an annular Halbach array. The permanent magnets 30 are held in spaced arrangement by a support 32 to form the annular Halbach array. By way of example, the support 32 may be constructed of plastic, fiberglass, or another suitable, preferably non-magnetic, material. The magnet assembly 12 may also include end-ring permanent magnets 34 arranged at the end of permanent magnets 30 for reducing the fall-off of the magnetic field at the ends of the magnet assembly 12.

The magnet assembly 12 may be configured to weigh no more than eighty kilograms, making it relatively light-weight and portable. Unlike clinical MRI systems, the magnet assembly 12 of the present invention is composed of permanent magnets; thus, it requires no cryogens. In other configurations of the magnet assembly 12 where a light-weight superconducting magnet may be used, cryogens may be required. However, because the homogeneity requirement of the magnetic field can be relaxed, the weight of such a superconducting magnet is significantly reduced compared to those superconducting magnets used in conventional clinical MRI systems.

An example of a magnet assembly 12 that may form a part of the portable MRI system 10 of the present invention is illustrated in FIGS. 2-5. As noted above, the magnet assembly 12 includes a plurality of permanent magnets 30 that are arranged in a Halbach array. A Halbach array arrangement is preferred because it creates a relatively uniform magnetic field without the need for a cryostat or power supplies. In some configurations, the magnet assembly 12 may include a light-weight superconducting magnet. The weight of such a magnet can be so reduced because the magnetic field of the superconducting magnet does not need to be as homogeneous as in conventional clinical MRI systems. Because of this relaxed homogeneity requirement, the weight of a superconducting magnet may be reduced significantly enough to be used in the magnet assembly 12 of the portable MRI system 10.

The magnet assembly 12 is designed to maximize the average magnetic field strength while allowing for small, controlled variations in the magnetic field for spatial encoding. Simulations such as COMSOL simulations may be used to optimize the magnetic field of the magnet assembly based on varying one or more parameters. Examples of parameters that can be varied in the magnet design include the size and quantity of the magnets 30; the size of the magnet assembly 12; and the addition of smaller rings for end field correction, such as end-ring magnets 34.

The permanent magnets 30 are composed of a magnetic material, such as a magnetic metallic material, a composite magnetic material, or a rare-earth magnetic material. By way of example, the permanent magnets 30 may be composed of a rare-earth element materials, such as neodymium-iron-boron ("NdFeB"). The permanent magnets 30 are preferably shaped as rods that extend from a proximal end to a distal end along the longitudinal axis of the magnet assembly. In this instance, each permanent magnet 30 will preferably have a polygonal cross-section. For example, the cross-section of the permanent magnets 30 may be a square, rectangle, circle, hexagon, or the like.

By way of example, the magnet assembly 12 illustrated in FIGS. 2-5 includes rod-shaped permanent magnets 30 with a square cross-section. To form the Halbach array, each permanent magnet 30 is rotated about its longitudinal axis relative to other adjacent permanent magnets 30. For instance, the magnet assembly 12 may include twenty permanent magnets 30, with each permanent magnet rotated relative to adjacent permanent magnets 30. As illustrated in FIG. 3, this configuration results in a spatially rotating pattern of magnetization, which, in turn, results in the generation of a magnetic field in the center 36 of the magnet assembly 12 and the cancellation of the magnetic field near to zero on the exterior of the magnet assembly 12.

Figure 7:
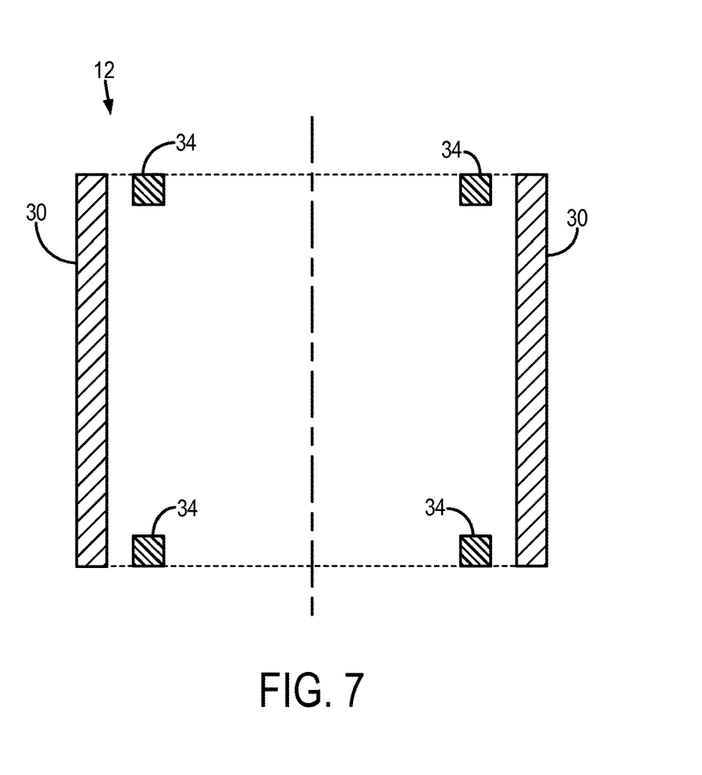
FIG. 7 is a cross-section of the configuration of permanent magnets of FIG. 7.

In this example, each of the twenty permanent magnets 30 is a radially magnetized NdFeB N42 magnet that is fourteen inches long and one inch-by-one inch square. The permanent magnets 30 may be placed into sleeves, such as fiberglass sleeves, to constrain them. The permanent magnets 30 may be forced into such sleeves using a compression jig and can be epoxied into place. Each of the sleeves may be oriented at the proper angle and held in place by the support 32. The support 32 may be composed of water-jet cut ABS plastic. The support 32 may include two end rings and a middle ring. As described above, an additional loop of one cubic inch end-ring magnets 34 may be arranged at each end of the permanent magnets 30, as illustrated in FIGS. 6 and 7. The end-ring magnets 34 reduce the fall-off of the magnet field at the ends of the magnet assembly 12, thereby improving the uniformity of the magnetic field along the longitudinal axis of the magnet assembly 12.

Figure 8:
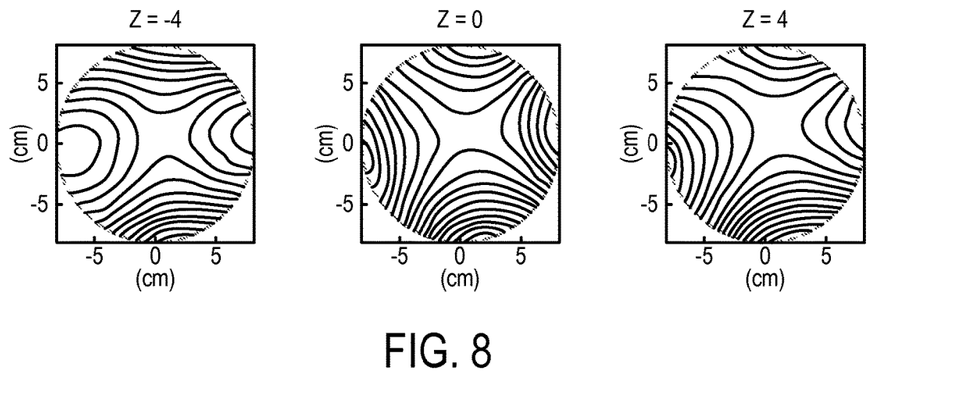
FIG. 8 is an example of magnetic field profiles generated by the magnet assembly of FIG. 2.
Figure 9:
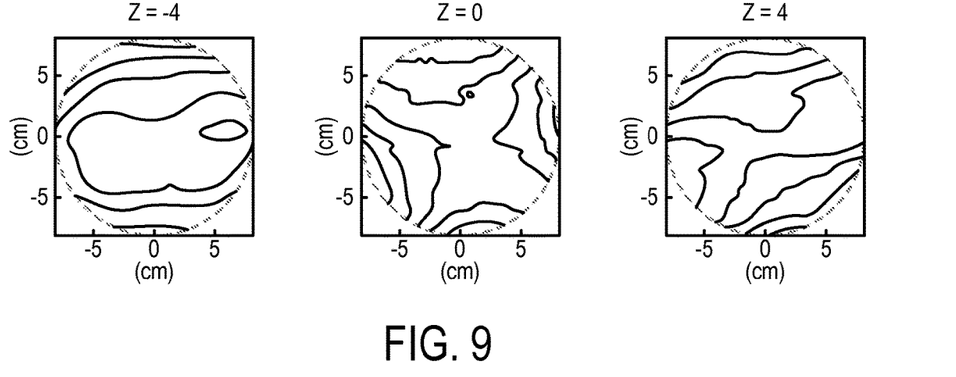
FIG. 9 is an example of magnetic field profiles generated by the configuration of permanent magnets in FIG. 6.

Referring now to FIGS. 8 and 9, an example of the in-plane magnetic field profile of the magnet assembly 12 of the portable MRI system 10 shown in FIG. 2 is illustrated. This magnetic field is transverse to the longitudinal axis of the magnet assembly 12; thus, when the portable MRI system 10 is used to image a patient's head, the magnet assembly 12 will produce a magnetic field with spatial variations suitable for spatial encoding in a plane perpendicular to the superior-inferior direction, or in oblique planes that are angled with respect to the transverse plane. FIG. 8 illustrates the field profile at three different longitudinal positions along the magnet assembly 12. These positions include the center of the magnet assembly 12, and four centimeters above and below the center of the magnet assembly 12. FIG. 9 illustrates the magnetic field profiles for the same magnet assembly 12 at the same longitudinal positions; however, the magnet field represented in FIG. 9 has been shimmed by the addition of additional magnets to the magnet assembly 12, such as by end-ring magnets 34.

The natural inhomogeneities of a magnet assembly 12 constructed in this manner are largely quadratic and well suited for spatially encoding magnetic resonance signals when rotated about the object being imaged into different measurement orientations. Moreover, the magnetic field profile of the magnet assembly 12 produces a central Larmor frequency for hydrogen protons of 3.3 MHz, which is suitable for imaging. While the homogeneity of the magnetic field generated by the magnet assembly 12 is well below that of superconducting magnets, the field shape allows for the inhomogeneities to be used for image encoding.

The inhomogeneous magnetic field of the magnet assembly 12 serves to polarize the object to be imaged and to readout magnetic resonance signals. The spatial position the readout magnetic resonance signals is then encoded by taking multiple measurements with the magnet assembly 12 rotated to different orientations around the object. For example, the first acquisition might have the $B_0$ field oriented transversely from left-to-right through the object. Then, the acquisition would be repeated with the magnet assembly 12 rotated in ten degree increments until thirty six different acquisitions, each with a unique magnetic field orientation, are obtained. The spatial inhomogeneities in the magnetic field generated by the magnet assembly 12 spatially modulate the magnetic resonance signal phase, thereby providing spatial encoding of the signals that can be used to reconstruct an image of the object. In this image reconstruction, detailed prior knowledge about the field profile for every orientation is used. For instance, image reconstruction is typically performed using an iterative algorithm to solve for the unknown image given complete knowledge of the encoding matrix.

The rotation of the magnet assembly 12 is accomplished by way of a rotator that is coupled to the support 32 of the magnet assembly 12. By way of example, the rotator may include a gantry coupled to the support 32 or a set of rollers on which the magnet assembly 12 rests and is allowed to roll about its longitudinal axis.

The spatial localization of magnetic resonance signals can be improved by using an array of RF receive coils. Information from the RF receive coil array may then be used to detect the signals in a process analogous to parallel imaging in conventional MRI. During reconstruction, the spatially varying coil sensitivities are incorporated directly into the encoding matrix. Further image encoding can also be achieved by limiting the bandwidth of the RF excitation pulse used. In this case, the excitation is limited to a constrained "onion-shell" of spatial regions. Still further improved spatial localization can be achieved by using the so-called "TRASE" method, in which a z-dependent spatial phase is applied using the RF transmit coil or coils.

The challenge with portable MRI systems is how to perform spatial encoding without the use of switched gradient coils. The present invention provides a system that does not require gradient coils. The lack of gradient coils offers numerous benefits, including lower power consumption, reduced complexity, the ability to use low-homogeneity and, therefore, light-weight permanent or superconducting magnets, and silent operation during imaging. A further discussion of spatial encoding with the portable MRI system 10 of the present invention is now provided.

transverse encoding is achieved as follows. The Halbach array configuration of the magnet assembly 12 naturally forms a nonlinear magnetic field whose variation in Larmor frequency (which varies about 50-100 KHz over the FOV) can be used for spatial encoding. The approximate shape of the magnetic field generated by the magnet assembly 12 illustrated in FIG. 2 is a second-order quadrupolar spherical harmonic, similar to a Patloc encoding field, which is described by J. Hennig, et al., in "Parallel imaging in non-bijective, curvilinear magnetic field gradients: a concept study," *MAGMA*, 2008; 21(1-2): 5-14. To take advantage of these variations for encoding, the magnet assembly 12 is rotated, either in discrete steps or continuously, and projections are acquired at each rotation angle. The readout direction is preferably selected to allow $\pi$ radians of relative phase to evolve between neighboring voxels near the periphery of the magnet assembly 12. Allowing too much phase to evolve will result in intravoxel dephasing. Thus, the readout duration is related to the reconstruction resolution achievable with the portable MRI system 10. To avoid aliasing, the sampling rate during readout should be set to be at least double the highest absolute spatial frequency occurring in the imaging field-of-view.

When the magnet assembly 12 and, thereby, its magnetic field is rotated in discrete steps, the resulting acquisition similar to that described by G. Schultz, et al., in "Radial imaging with multipolar magnetic encoding fields," *IEEE Trans Med Imaging*, 2011; 30(12):2134-2145; thus, the fast direct reconstruction described by Schultz is applicable to reconstruct images from k-space data acquired in this manner. It is noted, however, that the formalism described by Schultz differs in that it assumes perfect quadrupolar fields, whereas the magnet assembly 12 used in the portable MRI system 10 of the present invention may produce some linear and higher-order components.

One drawback to encoding with quadratic fields is that there is no encoding ability in the center of the magnet, where the magnetic fields are spatially flat. To mitigate this, linear terms can be generated in the magnetic field inhomogeneities. These linear terms can be generated, for example, by providing to the magnet assembly 12 a second array of permanent magnets in the next higher Halbach mode, which would form a linear field that could be rotated independently of the main magnet assembly 12. Note that if a traditional linear gradient term is applied with a second array of permanent magnets, conventional radial MR encoding can be used. In this configuration, after excitation, the k-space trajectory is a radial trajectory starting at isocenter. Application of a 180 pulse reverses the trajectory allowing it to pass thru the origin of k-space. Data acquisition then includes recording one linear projection per rotated position of the linear gradient magnet array.

Alternately, with no linear terms, the magnetic field can be offset from the isocenter of the head, so the "encoding hole" moves in a circular arc thru the head as the magnet is rotated. Rotating an offset field shape will remove the "encoding hole" in the center of the FOV.

Longitudinal encoding is achieved as follows. In one example, the method known as transmit array spatial encoding ("TRASE") may be used for longitudinal encoding. TRASE is described by J. C. Sharp and S. B. King in "MRI using radiofrequency magnetic field phase gradients," *Magn Reson Med,* 2010; 63(1):151-161, and by Q. Deng, et al., in "1D RF Phase Gradient Coil for TRASE RF Imaging," *Proc. ISMRM,* 2011; 1813. In the TRASE method, a linear phase imparted to the magnetization by an RF coil during excitation provides phase encoding along longitudinal direction. The linear phase is produced, for example, using a spiral birdcage coil or Maxwell/Helmholtz pairs to achieve the requisite 180 degree phase shift over the desired field-of-view. This linear phase can be defined as follows, $$B_1 = |B_1| e^{i\phi_1(r)} = 2\pi k_1 \cdot r = G_1 r \qquad (1).$$

This linear phase variation along the longitudinal direction imparts a k-space shift during RF excitation which does not depend on RF pulse shape. This requires a conventional constant-phase coil, or an array of coils, to be used for signal reception. If the same coil is used for transmit and receive, no net phase encoding is performed. Alternately 180 degree pulses can be applied with one coil and a second coil can be used to observe the spin refocusing in between 180 degree pulses, as in a normal echo train.

The TRASE method has synergy with the aforementioned transverse encoding in general because trains of multiple echoes will be required at each array rotation angle to obtain sufficient SNR. These same 180 degree pulses could be used for slice selection via TRASE encoding.

An alternative longitudinal encoding strategy is to use RF pulses with quadratic phase to isolate signals coming from the "vertex" of a parabola of RF-induced phase modulation, as described by J. G. Pipe in "Spatial encoding and reconstruction in MRI with quadratic phase profiles," *Magn. Reson. Med.,* 1995; 33(1):24-33, and by R. Chamberlain, et al., in "RASER: a new ultrafast magnetic resonance imaging method," *Magn. Reson. Med.,* 2007; 58(4):794-799. In the presence of a magnetic field gradient, the vertex of the parabola can be translated in a given direction. Away from the vertex, spins are dephased and contribute minimally to the acquired signal.

Another alternative method for longitudinal encoding is to use the natural variations of the magnetic field of the magnet assembly 12 along its longitudinal axis. The object being imaged can be excited with a hard pulse and frequency isocontours can be disambiguated in three dimensions, with additional spatial encoding provided by the surface coils in the receive array.

RF excitation in the portable MRI system 10 of the present invention is complicated by the fact that most spins are significantly off-resonance at all times, including while the RF transmit pulse is being played. To avoid phase and flip angle variation due to off-resonant spin precession during the RF pulse, the duration of the RF pulse should be set so as to achieve a sufficiently wide-band excitation. If the duration of the RF pulse must be longer due to limited available RF power, composite pulses can be designed to produce the same excitation phase for all frequencies across the object. An alternative approach is to use a suboptimal RF pulse and then incorporate the resulting spatially-varying phase into the encoding matrix during reconstruction.

A portable MRI system has been provided. The magnet assembly of the portable MRI system achieves reasonable homogeneity, but also provides inhomogeneities that are used to enable spatial encoding of magnetic resonance signals without the need for a gradient coil system. The portable MRI system can be constructed to weigh on the order of 45-80 kilograms and requires no power to maintain a magnetic field. In addition, the cost of building such a portable MRI system was only a few thousand dollars, making it a far less expensive alternative to traditional MRI systems. The accessibility of this portable MRI system has the potential to offer basic head trauma and hemorrhaging detection to a broad range of applications.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for acquiring magnetic resonance imaging data comprising:
   a) arranging an object within an inhomogeneous magnetic field relative to a rotation angle;
   b) generating a radio frequency (RF) field to the object to excite spins within the object;
   c) receiving magnetic resonance signals responsive to the generated RF field from the object;
   d) rotating the inhomogeneous magnetic field around the object to a different rotation angle to generate modulations in a phase of the magnetic resonance signals received from the object;
   e) repeating steps b) through d) a plurality of times to receive magnetic resonance signals from the object with a plurality of different rotation angles; and
   f) reconstructing an image of the object from the received magnetic resonance signals using the modulations in the phase of the magnetic resonance signals to determine spatial encoding of the magnetic resonance signals.

2. The method as recited in claim 1 in which step d) includes rotating an annular array of permanent magnets through one of discrete steps or continuous motion of different rotation angles to rotate the inhomogeneous magnetic field.

3. The method as recited in claim 1 in which step c) includes allowing n radians of relative phase to evolve between neighboring voxels acquire the imaging data while to controlling intravoxel dephasing when receiving the magnetic resonance signals.

4. The portable MRI system as recited in claim 3 in which the longitudinal encoding is achieved using one of a z-dependent spatial phase applied using the RF coil or RF pulses generated with the RF coil having a quadratic phase.

5. The method as recited in claim 1 further comprising generating a magnetic field offset applied relative to the inhomogeneous magnetic field.

6. The method as recited in claim 1 further comprising generating an RF field with a phase that varies linearly along a longitudinal axis of the object.

7. The method as recited in claim 1 further comprising encoding along a longitudinal axis of the object independently of rotating the inhomogeneous magnetic field.

8. The method as recited in claim 1 in which step c) includes controlling a bandwidth of RF field produced in step b) to create a series of constrained spatial regions and using the series of constrained spatial regions when reconstructing the image of the object in step f).

9. The method as recited in claim 8 in which step b) includes controlling against phase and flip angle variation due to off-resonant spin precession.

10. The method as recited in claim 8 in which step f) includes reconstructing the image of the object using an iterative reconstruction process.

11. A portable magnetic resonance imaging ("MRI") system, comprising:
a magnet assembly comprising:
a longitudinal axis along which a static magnetic field having inhomogeneities is formed;
a controller configured to:
receive magnetic imaging data acquired from an object arranged along the longitudinal axis as a position of the inhomogeneities of the static magnetic field is moved around the longitudinal axis; and
reconstruct the imaging data by spatially decoding the imaging data using the position of the inhomogeneities of the static magnetic field as it is moved around the longitudinal axis.

12. The portable MRI system as recited in claim 11 in which the magnet assembly includes a plurality of magnets and a support configured to hold the magnets in an annular Halbach array arrangement about the longitudinal axis.

13. The portable MRI system as recited in claim 11 in which the magnet assembly further comprises a plurality of end-ring magnets and a support configured to hold the plurality of end-ring magnets in an annular arrangement that is coaxial with the longitudinal axis.

14. The portable MRI system as recited in claim 13 in which the magnet assembly further comprises:
another plurality of magnets, each extending from a proximal end to a distal end along the longitudinal axis of the magnet assembly;
another support that is configured to hold the another plurality of magnets in an annular arrangement that is coaxial with the longitudinal axis such that the another plurality of magnets generate a linear magnetic field that augments the magnetic field generated by the plurality of magnets.

15. The portable MRI system as recited in claim 14 in which the another support is configured to rotate independently of the support and further comprising a rotator coupled to the another support and configured to rotate the another plurality of magnets about the longitudinal axis through a plurality of different rotation angles.

16. The portable MRI system as recited in claim 15 in which the controller is configured to control the rotator and an RF coil to allow radians of relative phase to evolve between neighboring voxels near at least a periphery of the magnet assembly to acquire the imaging data from the object arranged along the longitudinal axis.

17. The portable MRI system as recited in claim 15 in which the controller is configured to control the rotator and the RF coil to control intravoxel dephasing when acquiring the imaging data.

18. The portable MRI system as recited in claim 11 in which the magnet assembly is configured to produce both linear and higher-order components to create the static magnetic field having inhomogeneities.

19. The portable MRI system as recited in claim 11 further comprising at least one of a magnetic field linear gradient or an offset applied to the static magnetic field having inhomogeneities to provide spatial encoding proximate to the longitudinal axis of the magnet assembly.

20. The portable MRI system as recited in claim 11 further comprising a radio frequency (RF) coil configured to generate an RF field whose phase varies along the longitudinal axis of the magnet assembly.

21. The portable MRI system as recited in claim 11 further comprising a radio frequency (RF) coil configured to encode along the longitudinal axis of the magnet assembly independently of encoding by the magnet assembly.

22. The portable MRI system as recited in claim 11 in which the magnet assembly is further configured to generate the static magnetic field to vary along the longitudinal axis of the magnet assembly.

23. The portable MRI system as recited in claim 11 in which the controller is configured to control an array of RF coils and using information about spatially varying coil sensitivities to reconstruct an image of the object.

24. The portable MRI system as recited in claim 11 further comprising:
a rotator coupled to the magnet assembly and configured to rotate the magnet assembly about the longitudinal axis through a plurality of different rotation angles;
a radio frequency (RF) coil for generating RF energy and receiving magnetic resonance signals from an object positioned in the magnet assembly.

25. The portable MRI system as recited in claim 24 in which the controller is configured to control a bandwidth of RF excitation pulses produced by the RF coil to create a series of constrained spatial regions and use the series of constrained spatial regions when reconstructing the image of the object.

26. The portable MRI system as recited in claim 24 in which the controller is configured to acquire the imaging data with longitudinal encoding.

27. The portable MRI system as recited in claim 26 in which the longitudinal encoding is achieved using one of a z-dependent spatial phase applied using the RF coil or RF pulses generated with the RF coil having a quadratic phase.

28. The portable MRI system as recited in claim 24 in which the controller is configured to control the RF coil to control against phase and flip angle variation due to off-resonant spin precession.

29. The portable MRI system as recited in claim 11 in which the controller is configured to reconstruct an image of the object by correlating known spatial inhomogeneities of the static magnetic field having inhomogeneities with modulations in a phase of the magnetic resonance signal to determine spatial encoding information in the imaging data.

30. The portable MRI system as recited in claim 11 in which the controller is configured to reconstruct an image of the object using an iterative reconstruction process.

* * * * *

UNITED STATES PATENT AND TRADEMARK OFFICE
CERTIFICATE OF CORRECTION

PATENT NO. : 10,359,481 B2
APPLICATION NO. : 14/408187
DATED : July 23, 2019
INVENTOR(S) : Lawrence L. Wald et al.

Page 1 of 1

It is certified that error appears in the above-identified patent and that said Letters Patent is hereby corrected as shown below:

In the Specification

Column 6, Line 31, "transverse" should be --Transverse--.

In the Claims

Column 8, Line 64, Claim 3, "allowing n radians" should be --allowing $\pi$ radians--.

Signed and Sealed this
Tenth Day of September, 2019

Andrei Iancu
*Director of the United States Patent and Trademark Office*